(12) United States Patent
Colyar et al.

(10) Patent No.: US 10,487,274 B2
(45) Date of Patent: Nov. 26, 2019

(54) INTEGRATED COAL LIQUEFACTION, PETROLEUM OR BIOMASS FACILITY WITH DECREASED CARBON DIOXIDE PRODUCTION AND HIGHER CARBON AND THERMAL EFFICIENCIES

(71) Applicant: Axens North America Inc., Princeton, NJ (US)

(72) Inventors: James J Colyar, Pipersville, PA (US); John E Duddy, Langhorne, PA (US); Eric D Peer, Green Brook, NJ (US)

(73) Assignee: Axens, Rueil-Malmaison (FR)

( * ) Notice: Subject to any disclaimer, the term of this patent is extended or adjusted under 35 U.S.C. 154(b) by 11 days.

(21) Appl. No.: 15/910,069

(22) Filed: Mar. 2, 2018

(65) Prior Publication Data

US 2019/0270942 A1    Sep. 5, 2019

(51) Int. Cl.
| | |
|---|---|
| *C10G 65/12* | (2006.01) |
| *C01B 3/34* | (2006.01) |
| *C07C 29/15* | (2006.01) |

(52) U.S. Cl.
CPC ............... *C10G 65/12* (2013.01); *C01B 3/34* (2013.01); *C07C 29/15* (2013.01); *C01B 2203/0216* (2013.01); *C01B 2203/061* (2013.01); *C01B 2203/065* (2013.01); *C01B 2203/1241* (2013.01); *C10G 2400/02* (2013.01); *C10G 2400/04* (2013.01)

(58) Field of Classification Search
CPC .... C10G 65/12; C10G 29/15; C10G 2400/04; C10G 2400/02; C01B 3/34; C01B 2203/065; C01B 2203/061; C01B 2203/0216; C01B 2203/1241; C07C 29/15
See application file for complete search history.

(56) References Cited

U.S. PATENT DOCUMENTS

2011/0290703 A1* 12/2011 Colyar ............... B01D 53/62
208/400

OTHER PUBLICATIONS

Mar Perez-Fortes et al ; Methanol synthesis using captured CO2 as raw material: Techno-economic and environmental assessment; Jan. 2016, Applied Energy, vol. 161, pp. 718-732 (Year: 2016).*

* cited by examiner

*Primary Examiner* — Randy Boyer
*Assistant Examiner* — Juan C Valencia

(57) ABSTRACT

The integration of hydrogen and methanol production within a coal liquefaction, petroleum refinery or biomass conversion facility resulting in the unanticipated benefits of lower carbon dioxide ($CO_2$) production, net emissions, and higher carbon and thermal efficiencies is the subject of this invention.

7 Claims, 1 Drawing Sheet

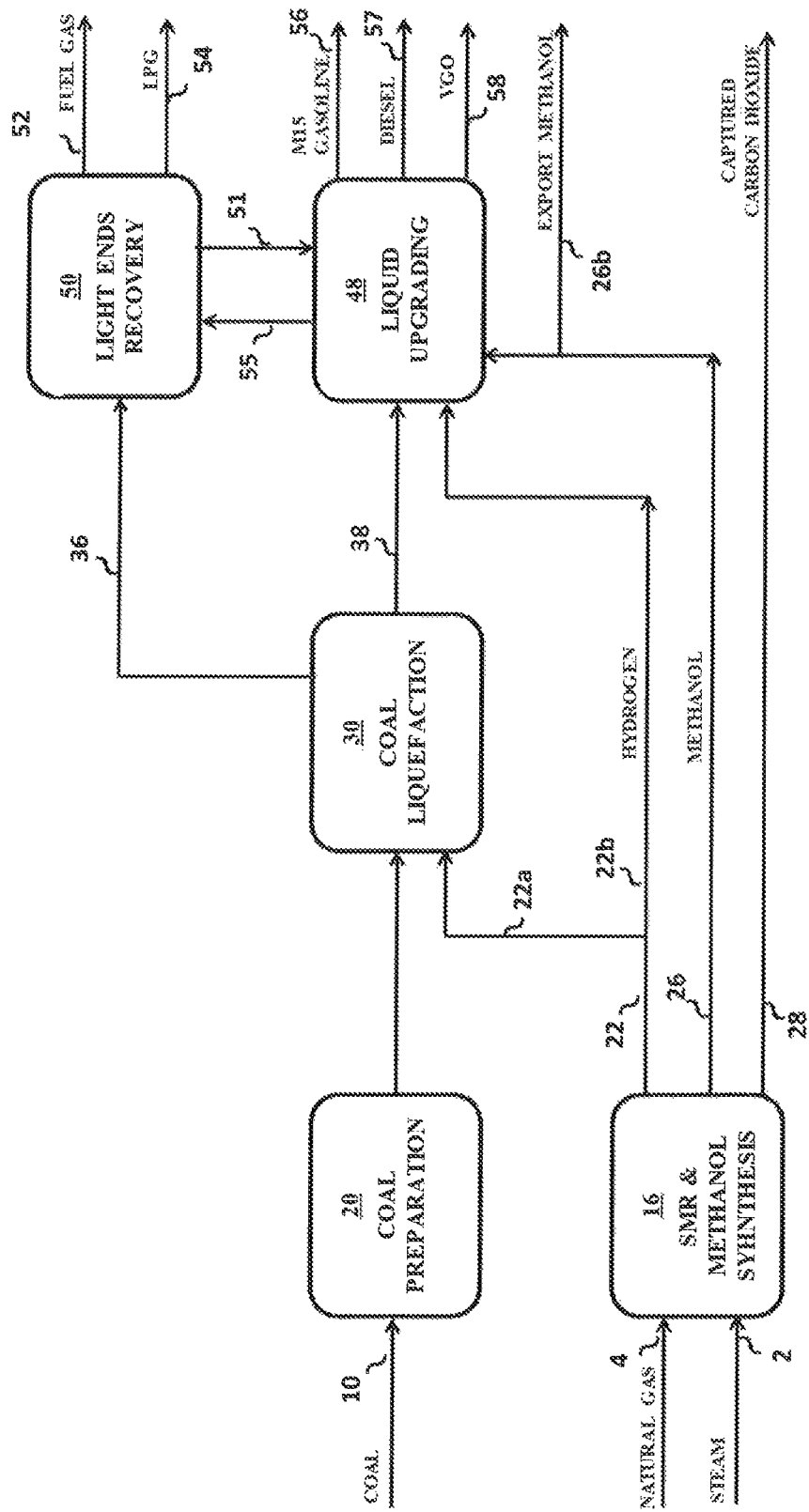

INTEGRATED COAL LIQUEFACTION, PETROLEUM OR BIOMASS FACILITY WITH DECREASED CARBON DIOXIDE PRODUCTION AND HIGHER CARBON AND THERMAL EFFICIENCIES

The integration of hydrogen and methanol production within a coal liquefaction, petroleum refinery or biomass conversion facility resulting in the unexpected benefits of lower carbon dioxide ($CO_2$) production as well as higher carbon and thermal efficiencies is the subject of this invention.

Applicants had the insight to recognize that there are many advantages in having a hydrogen plant integrated with a methanol plant within a coal liquefaction, petroleum refinery or biomass conversion facility to provide the required hydrogen for cracking/upgrading and the methanol required at the refinery for production of M15 gasoline, for example.

The invention involves the steam methane reforming (SMR) of natural gas and the judicious use of the raw syngas for the production of both methanol and high purity hydrogen. In the refinery, coal liquefaction or biomass facility, the hydrogen is utilized in the primary and secondary upgrading units. In these facilities, the methanol can be used to produce a hybrid light fuel including as M15 gasoline and/or can be exported as a fuel product blending or a petrochemical feedstock.

Applicant's innovative processing configuration results in several unforeseen advantages over the prior art. First, the integration of the hydrogen/methanol plant in the conversion facility results in a reduction of the quantity of $CO_2$ produced per unit of net liquids produced. Moreover, this integrated process improves the carbon efficiency (fraction of feed carbon to liquid products) as well as the thermal efficiency (fraction of feedstock heating value to liquid products).

Additionally, relative to a state-of-the-art coal liquefaction facility which utilizes the gasification of fresh and unconverted coal for producing the required hydrogen, the application of the processing configuration of Applicant's invention results in a significant increase in carbon efficiency, project net revenues, and the project internal rate of return (IRR).

The unique processing configuration is also an optimized method where the carbon in the feed coal and natural gas feedstock is most effectively utilized as evidenced by a reduction in the $CO_2$ produced and increases in the carbon and thermal efficiencies. Additionally, the specification of a once-through methanol synthesis plant to take advantage of the large raw syngas rate results in reduced capital and operating costs. Finally, Applicant's process configuration maximizes gasoline product rate via production of M15 and net methanol production which also contributes to the improved carbon utilization, plant thermal efficiency, high liquid yield, and enhanced project revenues and profitability.

More specifically, Applicant's herein teach an integrated process for simultaneously reducing carbon dioxide ($CO_2$) production and net carbon dioxide emissions while improving the carbon and thermal efficiencies of a heavy hydrocarbon processing facility comprising:

(a) producing a high purity hydrogen stream and a methanol stream using a steam methane reformer and once-through methanol production unit;

(b) feeding a portion of said hydrogen stream to a hydrocracking unit that is processing a heavy hydrocarbon stream to create a liquids stream;

(c) feeding a portion of said methanol stream and a portion of said hydrogen stream from step a) along with said liquids stream from step b) to a liquids upgrading unit to create one or more saleable petroleum streams.

BRIEF DESCRIPTION OF THE DRAWINGS

FIG. 1 shows a block flow diagram for the invention using a coal liquefaction facility as an example to illustrate Applicant's invention.

DETAILED DESCRIPTION OF THE INVENTION

FIG. 1 illustrates Applicant's processing configuration as applied in a coal liquefaction facility.

Feed coal 10 is fed to coal preparation 20 for drying and sizing and then to the direct coal liquefaction complex 30, which includes one or more coal liquefaction reactors. Direct coal liquefaction (DCL) is a process that reacts coal 10 in a solvent (not shown) with hydrogen at high temperature and pressure to produce liquid fuels. In the coal liquefaction complex 30, the coal is converted using a solid extrudate catalyst (not shown) and hydrogen 22a to raw liquid 38 and gaseous 36 products. The aforementioned hydrogen stream 22a for the coal liquefaction unit is created in a steam methane reformer and methanol synthesis complex 16.

Reforming of natural gas with steam is referred to as steam methane reforming (SMR) and is an efficient and effective method of producing commercial bulk hydrogen. In Applicant's invention the steam methane reformer and methanol synthesis complex 16 comprises a steam reformer reactor unit (not shown), a furnace section (not shown), and a methanol production unit. Details concerning the steam methane reformer and methanol synthesis complex 16 are not shown in FIG. 1 but can be described as follows.

The steam methane reformer reactor unit operates at high temperatures (700-1100° C.) and in the presence of a metal-based catalyst. In the steam reformer reactor unit, a steam stream 2 reacts with the hydrocarbons in the natural gas 4 to yield carbon monoxide and hydrogen according to the following formula:

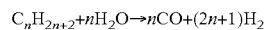

$$C_nH_{2n+2}+nH_2O \rightarrow nCO+(2n+1)H_2$$

Other reactions occurring in the steam reformer reactor unit include the water gas shift according to the formula:

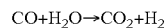

$$CO+H_2O \rightarrow CO_2+H_2$$

The primary SMR reaction is highly endothermic and requires high temperatures to obtain acceptable methane conversion rates. The large energy requirement for the SMR process is obtained from combustion reactions occurring in the furnace section of the steam reformer complex. The product from the steam reformer reactor unit is a synthetic gas stream, also known as syngas (not shown) containing primarily CO, $CO_2$, $H_2$, $H_2O$ and unreacted $CH_4$.

The raw SMR syngas is routed to a methanol production unit where the carbon monoxide and carbon dioxide react, using a catalyst, to produce methanol and water. The reaction is exothermic and excess energy can be used to reduce the SMR reactor fuel requirements. Consistent with the high rate of synthesis gas due to the relatively large amount of hydrogen consumed in the subject invention, the methanol synthesis plant is once-through (i.e., no recycle).

The purge syngas from the methanol plant, containing the same components as in the SMR raw gas, is routed to the shift conversion unit. In the shift unit, the carbon monoxide is shifted to hydrogen with accompanying additional carbon dioxide production. The product gas from the shift conversion unit is sent to the carbon dioxide removal unit which selectively adsorbs carbon dioxide 28 from the gas. The hydrogen-rich product from the $CO_2$ adsorber unit is further purified in a final membrane or adsorption unit resulting in hydrogen product 22. The hydrogen 22 gas contains in excess of 99 V % hydrogen and is thereafter available for use in the primary conversion and secondary upgrading units. The carbon dioxide stream 28 is thereafter further purified and compressed and is a final product.

A portion of the methanol 26 and a portion of the hydrogen 22b from the SMR/Methanol complex 16 is routed, along with liquid products 38 from the coal liquefaction complex 30 to the liquid upgrading unit 48 to produce saleable fuel products including, for example, M15 gasoline, 56, diesel 57, and vacuum gas oil (VGO) 58 products. The portion of the methanol stream 26 not utilized in the liquid upgrading unit 48 is exported 26b as a final product.

The raw gaseous products 36 from the coal liquefaction complex 30 are sent, along with raw gaseous products 55 from the liquid upgrading plant 48 to a light ends recovery unit 50 to produce, for example, fuel gas 52 and liquefied petroleum gases (LPG) 54, including propane, butane and mixtures thereof for use as refining fuel or as net products. Heavier components recovered in the light ends recovery section 50, shown as stream 51 are blended back to the liquid upgrading unit 48, primarily for M15 gasoline production.

This invention will be further described and understood by the following example case, which should not be construed as limiting the scope of the invention.

EXAMPLE

Direct Coal Liquefaction Study

A U.S. based direct coal liquefaction facility was studied to illustrate the advantages of the invention. The commercial size facility processes 8,000 MTPD (dry basis) of a bituminous coal to produce saleable liquid fuels. Three commercial cases were developed to estimate overall plant yields and economics including profitability. The first two cases (1 and 2) do not have any methanol production. In all cases, the coal is liquefied in a high pressure, high temperature ebullated-bed reactor system and the products are treated to be saleable. Electric power is imported in all cases except Case 1 where power is generated in the facility. A portion of the carbon dioxide from the SMR or gasifier (used in Case 1 only) is captured, purified and compressed.

The three cases are described below:

Case 1—The hydrogen requirements for the primary conversion and hydrotreating units are provided by the steam-oxygen gasification of the unconverted coal from the liquefaction unit and additional fresh coal. There is no methanol production. There is no SMR unit. An air separation plant is included with this case to produce the oxygen for the gasifier.

Case 2—The hydrogen requirements are provided by a natural gas fed SMR instead of the gasifier. There is no methanol production. The direct coal heavy residue, including unconverted coal and ash, is sent to the plant's battery limits for sale as a fuel.

Case 3—This case is the same as Case 2 except that the SMR raw gas is first routed to methanol production. This is the process configuration which utilizes the Applicant's invention. The production rate of methanol product is sufficient to provide a M15 gasoline product and methanol export.

The technical and economic results of the commercial study are summarized in Tables 2 and 3. Important assumptions are shown in Table 1 below.

TABLE 1

Important Assumptions

| Item | Units | Value |
| --- | --- | --- |
| Timeframe | — | 2017 |
| Operation per Year | Days | 330 |
| Construction Period | Years | 3 |
| Coal Cost | $/Short Ton | 27 |
| Light Oil (Brent) Price | $/Bbl | 70 |
| Natural Gas Price | $/MM Btu | 2.5 |
| Power Cost | $/Kw-Hr | 0.055 |
| Methanol Value | $/Bbl | 47 |

The two base cases (1 and 2) illustrate the difference between SMR and gasification for the production of the required hydrogen. The carbon dioxide captured is higher for the gasification case, however the carbon efficiency (fraction of feed carbon to liquid products) is significantly lower (57 vs. 49%). The carbon emitted to the atmosphere is also much higher for the gasification case. The gasification case has higher investment and significantly lower IRR. The lower profitability, relative to SMR based hydrogen production, is typically evident at natural gas prices lower than approximately $10/MM Btu.

The production of M15 gasoline and export of excess methanol in Case 3 has a higher level of carbon efficiency than Case 2 (58.5 vs. 57.0%), indicating that the incremental production of methanol is an efficient use of natural gas and will result in lower carbon dioxide production per quantity of liquids produced. This is shown in Table 2 where the carbon dioxide emitted is expressed per 1000 barrel of liquid product, the carbon emissions are 8% lower (92.6 vs. 100.6 ST/1000 Bbl) for Case 3 relative to Case 2. This is a significant outcome of the invention. There is also a 1.4 percentage point increase in the overall plant thermal efficiency relative to Case 2.

Relative to Case 2, Case 3 has 21% higher liquids production. This due to 6,357 BPSD of methanol production with 1,968 BPSD used to produce M15 gasoline and 4,389 BPSD exported. As shown in Table 3, Case 3 has a significantly larger plant annual net margin ($516 vs. $416 MM) and a higher project profitability. These economic results are also important outcomes of the study.

TABLE 2

Technical Results

|  | Case 1 | Case 2 | Case 3 |
| --- | --- | --- | --- |
| Coal Feed, MF STPD |  |  |  |
| To Liquefaction | 8,000 | 8,000 | 8,000 |
| To Gasification | 3,022 | — | — |
| Net | 11,022 | 8,000 | 8,000 |
| Natural Gas Feed, MMSCFD | — | 74.2 | 98.3 |
| Power, kW | 0 | 98 | 100 |
| Liquids, BPSD |  |  |  |
| $C_3/C_4$ | 3,039 | 3,039 | 3,025 |
| Gasoline | 11,074 | 11,074 | 13,122 |
| Methanol in Gasoline | — | — | 1,968 |

TABLE 2-continued

Technical Results

|  | Case 1 | Case 2 | Case 3 |
|---|---|---|---|
| Diesel | 14,197 | 14,197 | 14,197 |
| VGO Fuel | 2,819 | 2,819 | 2,819 |
| Net Product Methanol | — | — | 4,389 |
| Total Liquids | 31,129 | 31,129 | 37,553 |
| Liquids, B/ST of Coal | 2.82 | 3.89 | 4.69 |
| Carbon Dioxide, STPD |  |  |  |
| Captured | 11,062 | 2,851 | 2,699 |
| Emitted | 3,591 | 3,131 | 3,476 |
| Total | 14,653 | 5,982 | 6,175 |
| Carbon Dioxide Emitted, |  |  |  |
| ST/1000 Bbl of Liquid | 115.4 | 100.6 | 92.6 |
| Carbon Efficiency - % Feed | 49.3 | 57.0 | 58.5 |
| Carbon to Liquid Products |  |  |  |
| Overall Thermal Efficiency, % | 59.4 | 73.7 | 75.1 |

TABLE 3

Economic Results

|  | Case 1 | Case 2 | Case 3 |
|---|---|---|---|
| Operating Cost, $MM/Yr |  |  |  |
| Fixed | 268 | 181 | 187 |
| Variable | 171 | 231 | 254 |
| Total | 439 | 414 | 441 |
| Revenues, $MM/Yr | 830 | 830 | 957 |
| Coal Feedstock Costs, $MM/Yr | 110 | 80 | 80 |
| Net Margin, $MM/Yr | 391 | 416 | 516 |
| Investment, $MM | 4,669 | 3,145 | 3,264 |
| % of Base | 100.0 | 67.4 | 69.9 |
| Pre-Tax IRR, % | 4.7 | 9.5 | 11.7 |
| Relative to Base, Abs % | — | +4.8 | +7.0 |

The invention described herein has been disclosed in terms of specific embodiments and applications. However, these details are not meant to be limiting and other embodiments, in light of this teaching, would be obvious to persons skilled in the art. Accordingly, it is to be understood that the drawings and descriptions are illustrative of the principles of the invention, and should not be construed to limit the scope thereof.

We claim:

1. A integrated process for simultaneously reducing carbon dioxide ($CO_2$) production and net $CO_2$ emissions while improving the carbon and thermal efficiencies of a heavy hydrocarbon processing facility comprising:
    (a) producing a hydrogen stream comprising greater than ninety-nine volume percent hydrogen and a methanol stream using a steam methane reformer and methanol production unit;
    (b) feeding a portion of said hydrogen stream to a hydrocracking unit that is processing a heavy hydrocarbon stream to create a liquids stream;
    (c) feeding a portion of said methanol stream and said hydrogen stream from step a) along with said liquids stream from step b) to a liquids upgrading unit to create one or more saleable petroleum streams.

2. The process of claim 1 wherein the hydrocarbon processing facility is a coal liquefaction plant.

3. The process of claim 1 wherein the hydrocarbon processing facility is a biomass plant.

4. The process of claim 1 wherein the hydrocarbon processing facility is a petroleum plant.

5. The process of claim 1 wherein the carbon emissions for the hydrocarbon processing facility as expressed per one thousand barrels of liquid product produced, are reduced by at least eight percent (8%) compared to a conventional heavy hydrocarbon processing facility without said methanol production unit used to produce said methanol stream.

6. The process of claim 1 wherein the carbon emissions for the hydrocarbon processing facility as expressed per one thousand barrels of liquid product produced, are reduced by at least five percent (5%) compared to a conventional heavy hydrocarbon processing facility without said methanol production unit used to produce said methanol stream.

7. The process of claim 1 wherein the carbon efficiency for the heavy hydrocarbon processing facility as expressed as the percentage of feed carbon to liquid product produced, is increased by at least one and one half percentage points (1.5%) compared to a conventional heavy hydrocarbon processing facility without said methanol production unit used to produce said methanol stream.

* * * * *